United States Patent [19]

Patelli et al.

[11] 4,031,211

[45] June 21, 1977

[54] ADRIAMYCIN ESTERS, THEIR PREPARATION AND USE

[75] Inventors: Bianca Patelli; Luigi Bernardi, both of Milan; Federico Arcamone, Nerviano (Milan); Aurelio di Marco, Milan, all of Italy

[73] Assignee: Societa Farmaceutici Italia S.p.A., Milan, Italy

[22] Filed: June 10, 1976

[21] Appl. No.: 694,656

[30] Foreign Application Priority Data

June 20, 1975 United Kingdom ............. 26271/75

[52] U.S. Cl. .................................. 424/180; 536/4; 536/17
[51] Int. Cl.² ................. A61K 31/70; C07H 15/24
[58] Field of Search .................. 536/17, 4; 424/180

[56] References Cited

UNITED STATES PATENTS 3,803,124  4/1974  Arcamone et al. .................. 536/17

Primary Examiner—Johnnie R. Brown
Attorney, Agent, or Firm—Hubbell, Cohen, Stiefel & Gross

[57] ABSTRACT

Disclosed are novel C-14 adriamycin esters which are useful in the treatment of certain tumors.

8 Claims, No Drawings

ADRIAMYCIN ESTERS, THEIR PREPARATION AND USE

BACKGROUND OF THE INVENTION

1. Field of the Invention

The present invention relates to novel adriamycin esters, a process for their preparation, and the uses thereof.

2. The Prior Art

U.S. Pat. No. 3,803,124, owned by the unrecorded assignee hereof, discloses the preparation of certain C-14 adriamycin esters of the formula:

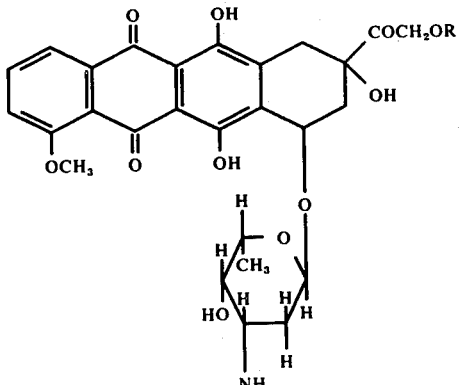

wherein R is an acyl radical of an acid selected from the group consisting of a substituted or unsubstituted, aliphatic mono- or dicarboxylic, aromatic, cycloaliphatic, arylaliphatic, heterocyclic acid having from 1 to 20 carbon atoms, the substituent being selected from the group consisting of halogens, hydroxyl, alkyl, alkoxy groups, free amino groups, mono- or dialkyl-substituted and nitro groups and from an alkyl- or aryl carbonic acid, from carbamic or alkylcarbamic acid and from sulfonic acid.

These esters of adriamycin are prepared according to said patent by reacting 14-bromo-daunomycin or one of its salts with a salt of the desired acid. More particularly, in accordance with the process of the invention, the 14-bromo-daunomycin or one of its salts such as the hydrochloride, is reacted with a compound of the formula ROM, wherein R is as defined above and M is an alkali or alkali earth metal or a quaternary ammonium radical eventually replaced by alkyl group. The reaction is carried out in the presence of an inert polar solvent, such as acetone, at the boiling temperature for a short time, or in the cold for a protracted reaction time. When the reaction is complete, the obtained product is isolated as such or is transformed into a salt of an inorganic or organic acid and purified by extraction and purification.

Said U.S. patent also discloses the preparation of 14-bromodaunomycin, which is one of the starting materials for the preparation of the novel esters of the present invention.

SUMMARY OF THE INVENTION

The present invention provides a new class of C-14 adriamycin esters of the formula (I):

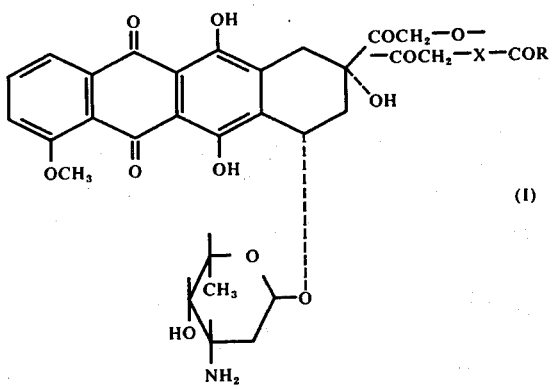

wherein X is O, S or NH and R is straight or branched alkyl or cycloalkyl having from 5 to 20 carbon atoms.

The invention also provides a process for the preparation of the above adriamycin esters and their acid addition salts, which process comprises reacting 14-bromodaunomycin or one of its salts, such as the hydrobromide, with a compound of the formula $RCOXCH_2COOM$, wherein R and X are as defined above and M is an alkali or alkaline earth metal, for example sodium, potassium and magnesium. The reaction is carried out in the presence of an inert polar solvent such as acetone, at the boiling temperature and for a short time. When the reaction is completed, the thus obtained product is isolated as such or is transformed into a salt of an inorganic or organic acid and purified by extraction and purification. In U.S. Pat. No. 3,803,124, it has been established that the C-14 adriamycin esters of that patent possess antitumor activity.

It has been subsequently demonstrated (J. Med. Chem. 17, 335, 1974) that the esterification of the C-14 hydroxyl group in adriamycin modifies the distribution of the esters in the human organs and that these esters are transformed in the body into adriamycin.

When compared with the previously reported adriamycin esters, it has been found that the new lipophilic esters according to the invention are metabolized, first to new, hydrophilic adriamycin esters of the formula (II):

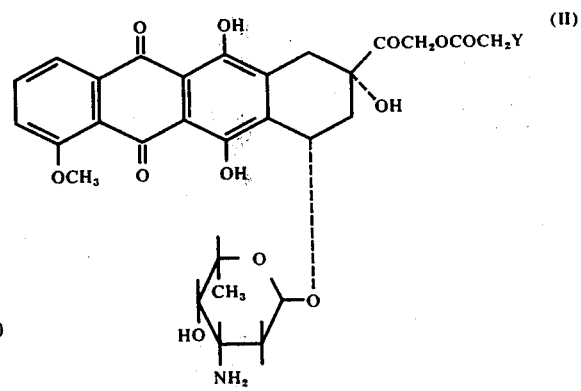

wherein Y is OH, SH or $NH_2$; which esters (II) are then hydrolyzed in the body into adriamycin, by a different mechanism, and this results in a better therapeutic action for the esters of the invention as compared with adriamycin.

Biological Activity of the New Adriamycin Esters of the Invention

The compounds according to the invention were tested on several in vitro systems and experimental mouse tumors, in comparison with adriamycin. The results reported in Table 1 show that on ascites sarcoma 180, adriamycin-14-0-stearoyl glycolate administered at doses equimolecular to the optimal adriamycin doses, exert an antitumor effect not significantly different from that of adriamycin.

On L 1210 leukemia and on Gross leukemia, adriamycin-14-0-stearoyl glycolate is as active as adriamycin, but less toxic. The activity on solid sarcoma 180 is reported in Table 2.

The activity of adriamycin-14-0-hexanoyl thioglycolate on ascites sarcoma 180 and on L 1210 leukemia is shown in Table 3.

On both tumors, the new ester exerts a marked antitumor effect, slightly lower than that of adriamycin, but is less toxic. The activity of adriamycin-14-0-hexanoyl glycolate is shown in Table 5. This compound is as active as adriamycin, but it is less toxic. The antitumor activity of adriamycin-14-0-lauroyl glycolate is shown in Table 5.

This compound causes a higher number of long term survivors that does adriamycin on ascites sarcoma 180 bearing mice; on L 1210 leukemia its activity is similar to that of adriamycin; on Gross leukemia this compound causes a higher increase of the median survival time than does adriamycin.

Moreover, this compound is less toxic than adriamycin.

The activity in vitro of the new 14-0-derivatives of adriamycin here described is reported in Table 6.

All the compounds are less cytotoxic than adriamycin and less active on Moloney Sarcoma Virus. The most active among all of them is adriamycin-14-0-lauroyl glycolate.

TABLE 1

Effect of adriamycin-14-0-stearoyl glycolate[1]

| Tumor | Schedule of Treatment Days[2] | Route | Adriamycin mg./kg. | TC[3] % | LTS[4] | TOX[5] | Adriamycin-14-0-stearoyl[1] glycolate mg./kg. | TC % | LTS | TOX |
|---|---|---|---|---|---|---|---|---|---|---|
| Ascites sarcoma 180 | 1 | ip |  |  |  |  | 0.3 | 119 | 1/10 |  |
|  |  |  | 1 | 243 | 3/10 | 0/10 | 1.6 | 222 | 2/10 | 1/10 |
|  |  |  | 5 | 150 | 3/10 | 0/10 | 7.8 | 187 | 1/10 | 1/10 |
| L 1210 leukemia | 1 | ip | 0.2 | 111 |  |  | 0.2 | 100 |  |  |
|  |  |  | 1 | 133 |  |  | 1 | 133 |  | 1/10 |
|  |  |  | 5 | 139 |  |  | 5 | 133 |  |  |
|  |  |  | 10 | 150 |  | 3/10 | 10 | 139 |  |  |
|  | 1 | ip | 10 | 139 | 1/10 | 1/10 | 10 | 128 |  |  |
|  |  |  | 12 | 167 |  | 2/10 | 12 | 150 |  |  |
|  |  |  | 15 | 100 |  | 6/10 | 15 | 150 |  |  |
| Gross Leukemia | 1,2,3 | iv | 3.5 | 143 |  | 1/10 |  |  |  |  |
|  |  |  | 4.5 | 171 |  |  | 4.5 | 143 |  | 1/10 |
|  |  |  | 6 |  |  | 4/10 | 6 | 186 |  |  |
|  |  |  |  |  |  |  | 7.5 | 186 |  |  |
|  |  |  |  |  |  |  | 9 | 207 |  |  |

[1]Dissolved in ethyl alcohol 5% in distilled water
[2]Days of treatment
[3]Median survival time as compared to untreated controls
[4]Long term survivors (> 60 days)
[5]Mice which showed toxic lesions at the autopsy

| Compound | Dose[1] (mg./kg.) | % tumor growth at day 11 | TOX |
|---|---|---|---|
| Adriamycin | 2.5 | 42 |  |
|  | 3 | 33 |  |
| Adriamycin-14-0-stearoyl glycolate | 2.5 | 58 |  |
|  | 3 | 58 |  |
|  | 3.5 | 52 |  |
|  | 4 | 37 | 1/10 |

[1]Treatment i.v. per 5 days

TABLE 3

Activity of adriamycin-14-0-hexanoyl thioglycolate[1]

| Tumor | Schedule of Treatment Days | Route | Adriamycin mg./kg. | TC % | LTS | TOX | Adriamycin-14-0-hexanoyl thioglycolate mg./kg. | TC % | LTS | TOX |
|---|---|---|---|---|---|---|---|---|---|---|
| Ascites sarcoma 180 | 1 | ip | 2 | 203 | 1/10 |  | 2 | 153 | 1/10 | 1/10 |
|  |  |  | 4 | 242 | 2/10 |  | 4 | 196 | 2/10 | 1/10 |
|  |  |  | 8 | 127 | 2/10 | 8/10 | 8 | 177 | 2/10 |  |
|  |  |  |  |  |  |  | 16 | 188 |  | 6/10 |
| L 1210 leukemia | 1 | ip | 2.5 | 122 |  |  | 4 | 133 |  |  |
|  |  |  | 5 | 155 |  |  | 8 | 155 |  |  |
|  |  |  | 10 | 233 | 2/9 | 2/9 | 16 | 170 | 2/9 |  |

[1]Dissolved in ethyl alcohol 5% in distilled water

TABLE 4

Antitumor effect of adriamycin-14-0-hexanoyl glycolate

| Tumor | Adriamycin mg./kg.[1] | TC[2] % | LTS[2] | TOX[2] | Adriamycin-14-0-hexanoyl glycolate mg./kg. | TC % | LTS | TOX |
|---|---|---|---|---|---|---|---|---|
| Ascites sarcoma 180 | 2 | 271 | 4/10 |  | 2 | 250 | 1/10 |  |
|  | 4 | 493 | 5/10 | 1/10 | 4 | 493 | 5/10 | 1/10 |
|  | 8 | 317 | 3/10 | 4/10 | 8 | 346 | 3/10 | 4/10 |
|  |  |  |  |  | 16 | 128 |  | 8/10 |
| L 1210 |  | 2.5 | 122 |  |  | 2 | 133 |  |

TABLE 4-continued

Antitumor effect of adriamycin-14-0-hexanoyl glycolate

| Tumor | Adriamycin | | | | Adriamycin-14-0-hexanoyl glycolate | | | |
|---|---|---|---|---|---|---|---|---|
| | mg./kg.[1] | TC[2] % | LTS[2] | TOX[2] | mg./kg. | TC % | LTS | TOX |
| leukemia | 5 | 155 | | | 4 | 144 | | |
| | 10 | 233 | 2/9 | 2/9 | 8 | 155 | 1/9 | |

[1]Treatment i.p. on day 1
[2]Days of treatment

TABLE 5

Effect of adriamycin-14-0-lauroyl glycolate

| Tumor | Schedule of Treatment | | Adriamycin[1] | | | | Adriamycin-14-0-lauroyl glycolate[2] | | | |
|---|---|---|---|---|---|---|---|---|---|---|
| | Days | Route | mg./kg. | TC % | LTS | TOX | mg./kg. | TC % | LTS | TOX |
| Ascites sarcoma 180 | 1 | ip | 2 | 271 | 4/10 | | 2 | 436 | 4/10 | 1/10 |
| | | | 4 | 493 | 5/10 | 1/10 | 4 | 493 | 8/10 | 1/10 |
| | | | 8 | 317 | 3/10 | 4/10 | 8 | 385 | | 1/10 |
| | | | | | | | 16 | 242 | | 9/10 |
| L 1210 leukemia | 1 | ip | 2.5 | 122 | | | 2 | 135 | | |
| | | | 5 | 155 | | | 4 | 141 | | |
| | | | 10 | 233 | 2/9 | 2/9 | 8 | 165 | | |
| | | | | | | | 16 | 200 | 1/10 | |
| Gross leukemia | 1,2,3 | iv | 3.5 | 157 | | | 4.5 | 136 | | |
| | | | 4.5 | 178 | | | 6 | 257 | 2/10 | |
| | | | | | | | 7.5 | 221 | | |
| | | | | | | | 9 | 128 | | 3/10 |
| | 1,2,3 | iv | 3.5 | 143 | | 1/10 | 6 | 193 | | |
| | | | 4.5 | 171 | | | 7.5 | 214 | | |

[1]Dissolved in ethyl alcohol 5% in distilled water
[2]Dissolved in Tween 80 10% in distilled water

TABLE 6

In vitro effects of 14-0-esters of adriamycin

| Compound | $ID_{50}$ (mg./ml.) | | |
|---|---|---|---|
| | Hela[1] | MSV[2] | MEF[3] |
| Adriamycin | 18 | 9 | 21 |
| Adriamycin-14-0-stearoyl glycolate | 100 | 12 | 60 |
| Adriamycin-14-0-hexanoyl glycolate | 85 | 35 | 110 |
| Adriamycin-14-0-hexanoyl thioglycolate | 175 | 28 | 60 |
| Adriamycin-14-0-lauroyl glycolate | 36 | 17 | 18 |

[1]Colony inhibition test (treatment per 24 hours)
[2]Inhibition of Moloney sarcoma virus-induced foci in mouse embryo fibroblasts proliferation (treatment per 72 hours)
[3]Inhibition of mouse embryo fibroblasts proliferation (treatment per 72 hours)

DESCRIPTION OF THE PREFERRED EMBODIMENTS

The following examples are given to illustrate the invention without, however, limiting it.

EXAMPLE 1

Adriamycin-14-0-Stearoyl Glycolate Hydrochloride

To 1 g. of 14-bromodaunomycin hydrobromide in 100 ml. of anhydrous acetone, 2.5 g. of potassium stearoyl glycolate were added and the suspension was refluxed for 3 hours. After filtration, the acetone solution was evaporated in vacuo, the residue was taken up in chloroform and washed with 5% $NaHCO_3$ and water. The chloroform solution was evaporated in vacuo and the residue chromatographed don silica gel, eluting first with chloroform, then with $CH_2Cl_2$ : $CH_3OH$ : $H_2O$ (100 : 20 : 2). Adriamycin-14-0-stearoyl glycolate was collected and converted into the hydrochloride by dissolving it in chloroform containing one equivalent of HCl.

Adding ethyl ether, adriamycin-14-0-stearoyl glycolate hydrochloride was precipitated and collected. m.p. 178–180° C., Rf 0.35 (daunomycin Rf = 0.20) in the system : chloroform : methanol : water (14 : 6 : 1). I.R. spectrum: 1740 cm$^{-1}$ (broad), 1620 and 1575 cm$^{-1}$ (sharp) (CO).

EXAMPLE 2

Adriamycin-14-0-Hexanoyl Glycolate Hydrochloride

Operating as in Example 1, but using 14-bromodaunomycin and potassium hexanoyl glycolate, adriamycin-14-0-hexanoyl glycolate, m.p. 190–192° C, Rf 0.30 was obtained; I.R. spectrum: 1740 cm$^{-1}$ (broad), 1620 and 1575 (sharp) (CO).

EXAMPLE 3

Adriamycin-14-0-Lauroyl Glycolate Hydrochloride

Operating as in Example 1, but using 14-bromodaunomycin and potassium lauroyl glycolate, adriamycin-14-0-lauroyl glycolate hydrochloride, m.p. 133–135° C; Rf 0.33 was obtained; I.R. spectrum: 1740 cm$^{-1}$ (broad); 1620 and 1575 (sharp) (CO).

EXAMPLE 4

Adriamycin-14-0-Hexanoyl Thioglycolate Hydrochloride

Operating as in Example 1, but using 14-bromodaunomycin and potassium hexanoyl thioglycolate, adriamycin-14-0-hexanoyl thioglycolate hydrochloride, m.p. 180–182° C.; Rf 0.31 was obtained; I.R. spectrum: 1735, 1695, 1620 and 1575 cm$^{-1}$ (sharp) (CO).

EXAMPLE 5

Adriamycin-14-0-Hexanoylglycinate Hydrochloride

Operating as in Example 1, but using 14-bromodaunomycin and potassium hexanoylglycinate, adriamycin-14-0-hexanoyl glycinate hydrochloride, m.p. 140–142° C.; Rf 0.30 was obtained.

Other compounds embraced by the formula (I) can likewise be prepared by the same procedure by simply substituting other suitable compounds of the formula RCOXCH₂COOM in the reaction.

Variations and modifications can, of course, be made without departing from the spirit and scope of the invention.

Having described our invention what we desire to secure by Letters Patent and hereby claim is:

1. An adriamycin ester of the formula (I):

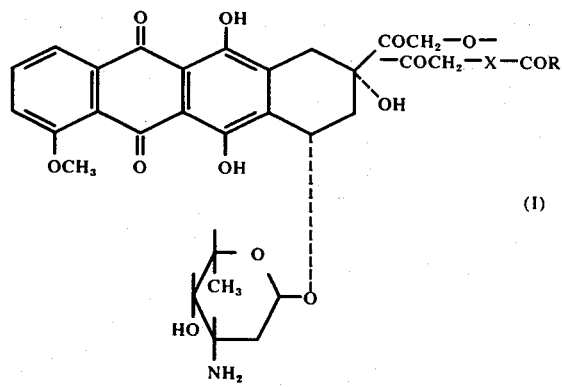

wherein X is O, S or NH and R is a straight chain alkyl having from 5 to 20 carbon atoms and the hydrochlorides thereof.

2. A compound according to claim 1, which is adriamycin-14-0-stearoyl glycolate or its hydrochloride.

3. A compound according to claim 1, which is adriamycin-14-0-hexanoyl glycolate or its hydrochloride.

4. A compound according to claim 1, which is adriamycin-14-0-lauroyl glycolate or its hydrochloride.

5. A compound according to claim 1, which is adriamycin-14-0-hexanoyl thioglycolate or its hydrochloride.

6. A compound according to claim 1, which is adriamycin-14-0-hexanoyl glycinate or its hydrochloride.

7. A method for inhibiting the growth of a tumor selected from the group consisting of ascites sarcoma 180, L 1210 leukemia, gross leukemia, solid sarcoma 180 comprising intravenously or intraperitoneally administering to a host afflicted with said tumor an amount of a compound according to claim 1, sufficient to inhibit the growth of said tumor.

8. A metabolic product of the formula

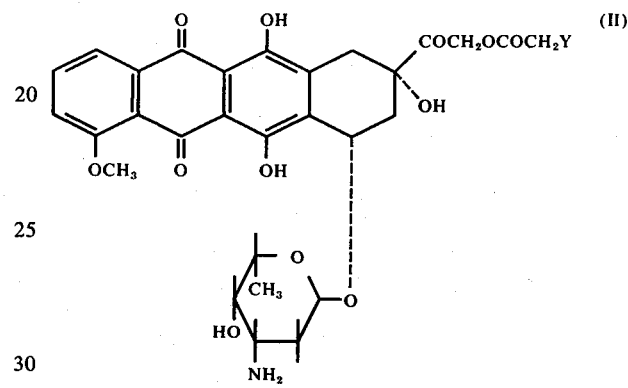

wherein Y is SH.

* * * * *

UNITED STATES PATENT OFFICE
CERTIFICATE OF CORRECTION

Patent No. 4,031,211　　　　　　　　　Dated June 21, 1977

Inventor(s) Bianca Patelli et al.

It is certified that error appears in the above-identified patent and that said Letters Patent are hereby corrected as shown below:

Column 3, line 42: "survivors that" should read -- survivors than --.

Columns 3-4, after Table 1: should read
　　　　　　　　　　TABLE 2
-- Activity of adriamycin-14-O-stearoyl glycolate on --.
　　solid sarcoma 180

Columns 3-4, Table 2, column 1, lines 3-4:
"stearoyl gly-　　　　　　　　　-- stearoyl glyco-
　late"　　　　should read　　　late --.

Column 5, line 59: "don" should read -- on --.

Signed and Sealed this

Eleventh Day of October 1977

[SEAL]

Attest:

RUTH C. MASON　　　　　　LUTRELLE F. PARKER
*Attesting Officer*　　　*Acting Commissioner of Patents and Trademarks*